(12) United States Patent
Spring

(10) Patent No.: US 6,480,347 B1
(45) Date of Patent: Nov. 12, 2002

(54) DEVICE FOR REPRODUCIBLE POSITIONING OF OPTICAL SURFACES

(75) Inventor: Erin D. Spring, Corfu, NY (US)

(73) Assignee: Leica Microsystems Inc., Depew, NY (US)

(*) Notice: Subject to any disclaimer, the term of this patent is extended or adjusted under 35 U.S.C. 154(b) by 0 days.

(21) Appl. No.: 09/661,355

(22) Filed: Sep. 14, 2000

(51) Int. Cl.[7] .................................................. G02B 5/04
(52) U.S. Cl. ...................... 359/831; 356/137; 356/136; 359/837; 73/864.91; 269/8; 248/206.5
(58) Field of Search ............................... 359/831, 837; 356/128–137, 226; 73/864.91; 269/8; 248/206.5

(56) References Cited

U.S. PATENT DOCUMENTS

| | | | |
|---|---|---|---|
| 3,770,352 A | 11/1973 | White | 356/133 |
| 4,650,323 A | 3/1987 | Nakagawa | 356/135 |
| 4,828,360 A * | 5/1989 | Maruyama | 359/824 |
| 5,306,467 A * | 4/1994 | Douglas-Hamilton et al. | 422/99 |

FOREIGN PATENT DOCUMENTS

| | | | |
|---|---|---|---|
| AT | 211070 | * | 9/1960 |
| JP | 09281000 A | | 10/1997 |

* cited by examiner

*Primary Examiner*—Cassandra Spyrou
*Assistant Examiner*—Arnel C. Lavarias
(74) *Attorney, Agent, or Firm*—Simpson & Simpson, PLLC

(57) ABSTRACT

A plurality of magnets is provided in an illumination prism carrier of a transmitted light refractometer and a corresponding plurality of magnets is provided in a sample prism housing of the refractometer to align a light exit surface of the illumination prism relative to a sample surface of the sample prism and urge the optical surfaces together in an even and uniform manner. The magnets replace mechanical biasing arrangements for positioning the optical surfaces and function to consistently reproduce a measurement optical path in the instrument for improved accuracy and repeatability of measurements.

6 Claims, 2 Drawing Sheets

DEVICE FOR REPRODUCIBLE POSITIONING OF OPTICAL SURFACES

BACKGROUND OF THE INVENTION

1. Field of the Invention

The present invention relates generally to devices for positioning one optical element relative to another optical element in an optical instrument, wherein selective relative movement between the optical elements is necessary for measurement purposes. More particularly, the present invention relates to a device for repeatably positioning a pair of optical surfaces, one from each optical element, opposite each other to consistently replicate an optical path in the instrument. The present invention is applicable, for example, to the field of refractometry and refractometers.

2. Description of the Related Art

Optical instruments for performing test measurements often require that an optical path be established that includes a test subject or sample in the optical path, whereby an effect of the test subject or sample on light traveling along the optical path can be observed. An important factor in the precision of such instruments (that is, the ability of the instrument to provide a reproducible measurement) is the consistency with which the optical elements defining the optical path are located relative to the test subject or sample and one another, especially where one or more optical elements are selectively movable temporarily away from a measurement position to allow the test subject or sample to be introduced in the optical path.

An example of this type of optical instrument is a transmitted light refractometer, such as an Abbe or Pulfrich refractometer used for measuring the refractive index of liquids. Transmitted light refractometers are known to include a prism assembly comprising an illumination prism cooperating with a sample prism. The sample prism has a sample surface for receiving a transparent or translucent test sample, and the illumination prism directs light from a light source to be obliquely incident at a known angle to the test sample, whereby the critical angle of total reflection at the interface between the sample and sample surface of the sample prism is directly or indirectly observed. Consequently, it is necessary for a light exit surface of the illumination prism to evenly contact the test sample.

In prior art refractometers of the type described above, the illumination prism is typically mounted in a hinged illumination prism carrier that opens pivotally to allow the sample to be placed on the sample surface and closes pivotally over the sample. A biasing load is applied by mechanical means or simple gravity to ideally provide a uniformly thin layer of sample liquid between the exit surface of the illumination prism and the sample surface of the sample prism, with the exit and sample surfaces ideally orientated parallel to one another.

U.S. Pat. No. 4,650,323 discloses a hand-held refractometer that includes a weight 29 on a movable plate 23 provided in the illumination prism carrier to apply a uniform vertical load to the sample liquid. See column 5, lines 36–47. This arrangement is well suited for a hand-held refractometer with relatively low precision and accuracy demands. However, play in the hinge mechanism and instrument tilt angle at the time of reading cause variations in the magnitude and line of action of the weight-induced biasing force that tends to bring the exit surface and sample surface together, which variations result in a wider scattering of measurement data for a series of measurements taken with respect to a constant test sample than is desired for applications where accuracy and precision demands are relatively high.

Heretofore, manufacturers of Abbe refractometers, such as Atago, Bellingham+Stanley, Spectronic Instruments, Milton Roy, and Leica Microsystems Inc. (assignee of the present invention) have relied on mechanical clips, friction locks, and cam locks operating between the illumination prism carrier and sample prism housing to apply a biasing force tending to bring the exit surface of the illumination prism and the sample surface of the sample prism together. However, there are limitations to such mechanical devices which have a detrimental effect on measurement accuracy and precision. First, the force is not arranged symmetrically with respect to the prism surfaces, whereby non-uniform sample thickness occurs. Second, the mechanical devices do not correct for small variations in the locational alignment of the exit surface relative to the sample surface due to play in the hinge mechanism. Third, mechanical devices with moving parts are subject to wear over time. In part because of these limitations, automatic Abbe refractometers of the prior art have not exceeded an accuracy on the order of $+/-0.0001$ for refractive index readings.

BRIEF SUMMARY OF THE INVENTION

Therefore, it is an object of the present invention to provide a device for positioning one optical surface relative to another optical surface in an optical instrument in a repeatable or reproducible manner.

It is another object of the present invention to provide a device that achieves reproducible positioning of optical surfaces without the use of mechanical clips, friction locks, cam, locks, or weights.

It is a further object of the present invention to provide a device that positions one optical surface closely adjacent and parallel to another optical surface by establishing a constant and symmetrically applied biasing force tending to bring the optical surfaces together, whereby a thin uniform optical layer can be achieved between the surfaces.

It is a further object of the present invention to provide a device that self-aligns and locates one optical surface relative to another optical surface.

It is a further object of the present invention to provide an improved prism assembly for refractometers that is easy to assemble and clean.

Pursuant to these and other objects, the present invention is embodied in a prism assembly of a refractometer having an illumination prism mounted for selective movement to and from a measurement position with respect to a sample prism. The sample prism is fixed in a housing and includes an exposed sample surface for receiving a liquid sample, and the illumination prism is mounted in a carrier hingedly connected to the refractometer such that a light exit surface of the illumination prism can be selectively positioned directly opposite and closely adjacent the sample surface. In a preferred embodiment, a plurality of magnets is set within recesses in the illumination prism carrier to be flush with an engagement surface of the carrier. The magnets are symmetrically arranged about the length and width of the rectangular exit surface. Likewise, a plurality of corresponding magnets is set within recesses in the sample prism housing carrier to be flush with an engagement surface of the housing. Each magnet in the carrier matches up and cooperates in attraction with a respective magnet in the housing when the prism assembly is in its measurement position.

The present invention improves instrument accuracy and precision by creating a uniformly thick layer of sample fluid between the light exit and sample optical surfaces due to a constant and repeatable biasing force urging the optical surfaces together. The magnets also serve to self-align the surfaces relative to one another to minimize detrimental misalignment due to play in the hinge mechanism for the carrier.

BRIEF DESCRIPTION OF THE SEVERAL VIEWS OF THE DRAWINGS

The nature and mode of operation of the present invention will now be more fully described in the following detailed description of the preferred embodiment taken with the accompanying drawing figures, in which.

DETAILED DESCRIPTION OF THE PREFERRED EMBODIMENTS

Figure 1:
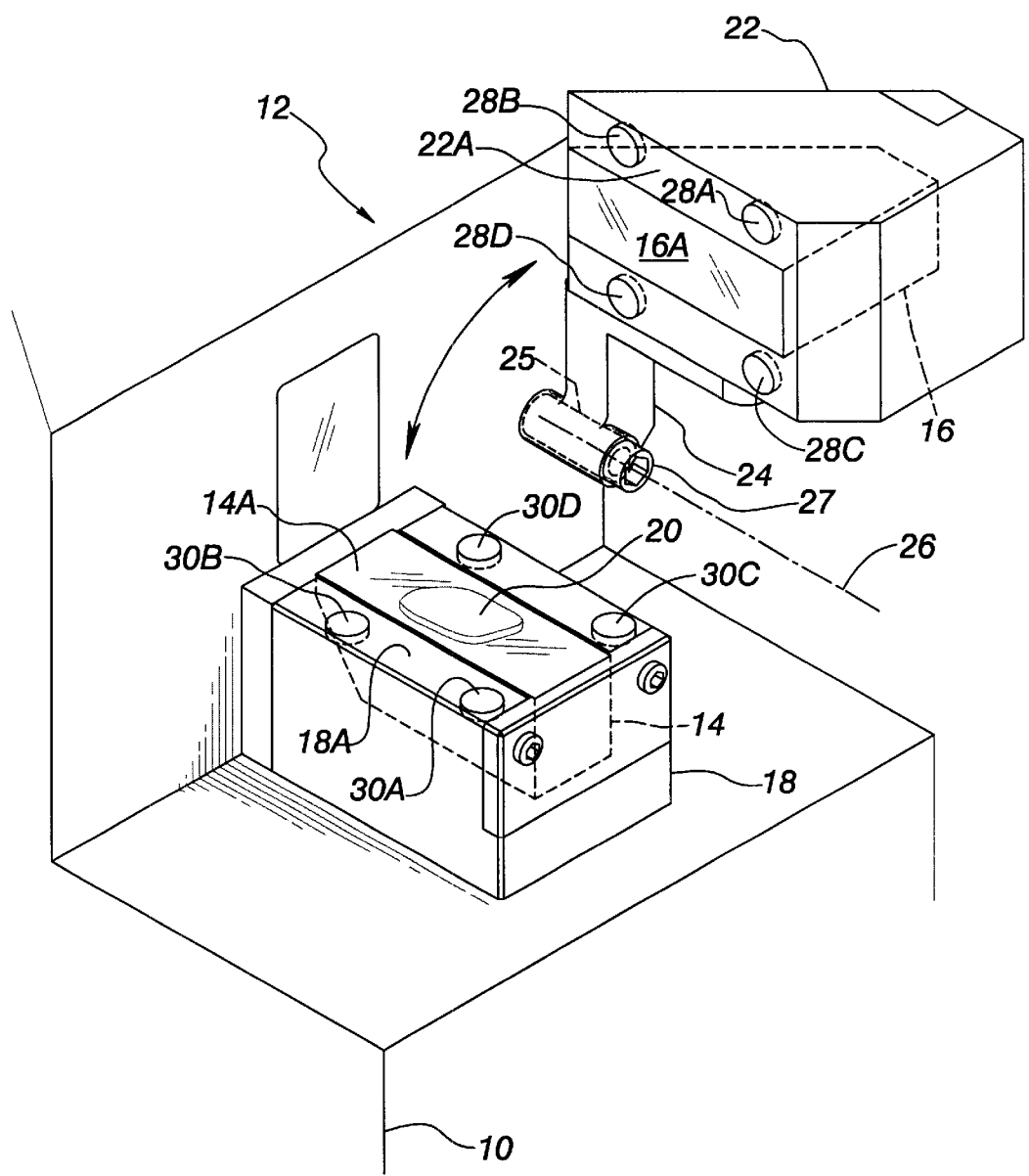
FIG. 1 is a perspective view of a refractometer prism assembly formed in accordance with a preferred embodiment of the present invention, shown in a preparation position.

Referring initially to FIG. 1 of the drawings, an optical instrument 10, namely a refractometer, comprises a prism assembly 12 that includes a sample prism 14 and an illumination prism 16. Sample prism 14 is secured within a sample prism housing 18 that is fixed to refractometer 10 such that a sample surface 14A of the sample prism is exposed and orientated horizontally for receiving a liquid test sample 20. Illumination prism 16 is secured within an illumination prism carrier 22 connected to refractometer 10 by a hinge arm 24 allowing selective pivotal motion of the illumination prism about a hinge axis 26. Illumination prism 16 includes a light exit surface 16A from which light generated by a light source (not shown) of the refractometer exits the prism to illuminate sample 20.

Figure 2:
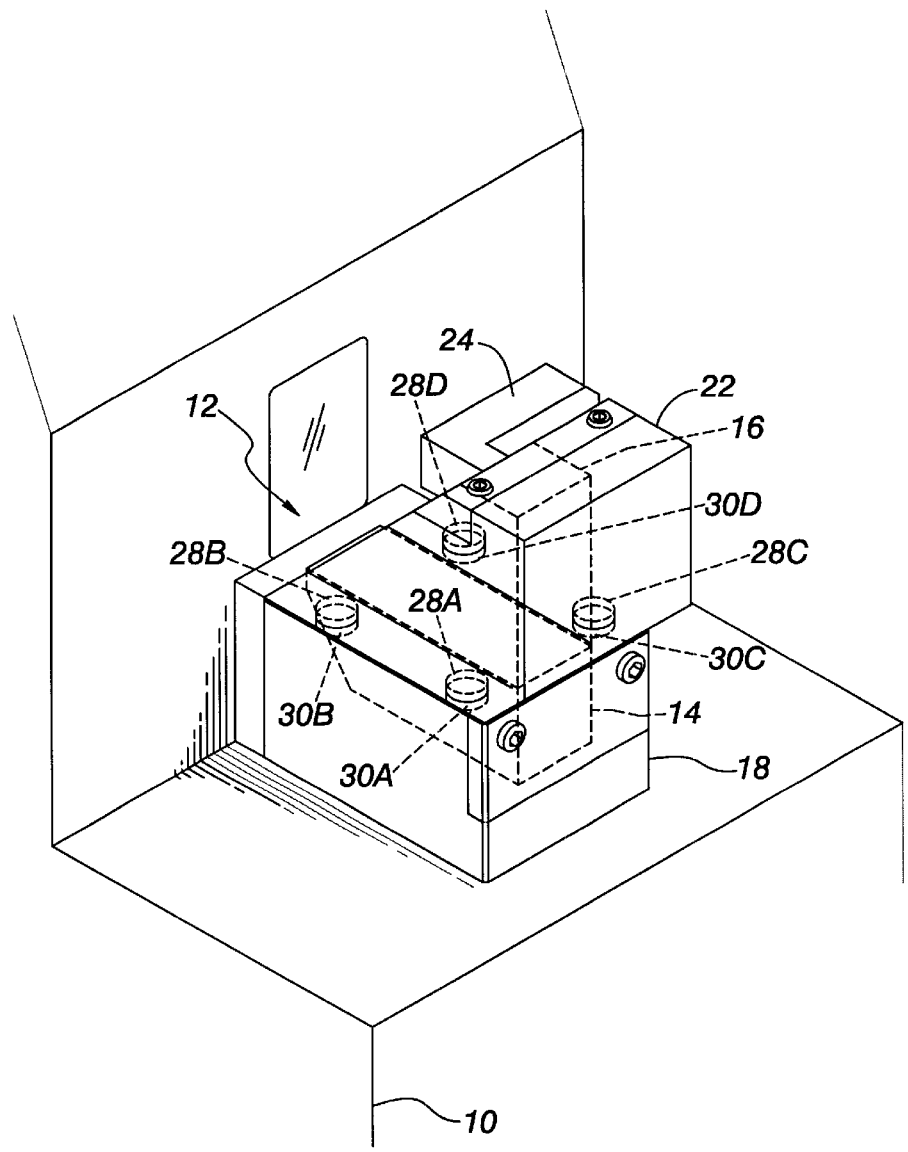
FIG. 2 is a view similar to that of FIG. 1, however showing the prism assembly in a measurement position.

In order to take a measurement, an operator places sample 20 on sample surface 14A while illumination prism carrier 22 is in a pivotal position, such as that shown in FIG. 1, where the carrier 22 does not interfere with sample placement. Then, the operator manually pivots the illumination prism carrier 22 about hinge axis 26 to bring exit surface 16A directly opposite and closely adjacent to sample surface 14A as depicted in FIG. 2. Hinge arm 24, illumination prism carrier 22, and sample prism housing 18 are designed so that an engagement surface 22A of carrier 22 is in complete flush contact with an engagement surface 18A of housing 18 in the measurement position. A very slight gap or spacing on the order of 0.003 to 0.004 inches (0.076 to 0.102 mm) is specified between exit surface 16A and sample surface 14A in the measurement position. Consequently, sample 20 is spread out to form a thin layer between illumination prism 16 and sample prism 14. The purpose of the arrangement is to provide an optical path sequentially from illumination prism 16 through sample 20 to sample prism 14 without any air gaps and ideally with exit surface 16A parallel to sample surface 14A. Up to this point, the description of refractometer 10 is consistent with known prior art.

The present invention departs from the prior art in that the exit surface 16A of illumination prism 16 and the sample surface 14A of sample prism 14 are magnetically biased toward one another. In the preferred embodiment described herein, magnetic biasing means is in the form of four magnets 28A–28D provided in illumination prism carrier 22 and four corresponding magnets 30A–30D provided in housing 18. In the arrangement shown, two magnets are located on each of two opposite sides of exit surface 16A, and two magnets are located on each of two opposite sides of sample surface 14A, thereby creating a symmetrical force distribution about the length and width of the optical surfaces. When prism assembly 12 is in the measurement position shown in FIG. 2, magnets 28A and 30A are directly opposite each other, magnets 28B and 30B are directly opposite each other, magnets 28C and 30C are directly opposite each other, and magnets 28D and 30D are directly opposite each other. Magnets 28A–28D are set within respective recesses in carrier 22 slightly below engagement surface 22A and fixedly sealed with epoxy. After the epoxy has cured, engagement surface 22A is lapped flush with the epoxy. Likewise, magnets 30A–30D are set within respective recesses in housing 18 slightly below engagement surface 18A and fixedly sealed with epoxy, and engagement surface 18A is lapped flush with the cured epoxy. Finally, a master magnet is used to set proper pole orientation of magnets 28A–28D and magnets 30A–30D. Since attractive magnetic force is desired under the present embodiment, the pole orientations of corresponding magnet pairs 28A/30A, 28B/30B, 28C/30C and 28D/30D are set such that opposite poles are aligned in the measurement position.

In order to fully realize the benefits of the magnetic biasing arrangement of the present invention, hinge arm 24 is mounted during assembly of the refractometer and then tightened after carrier 22 is positioned at a best fit location relative to housing 18. More specifically, a sleeve 25 has an outer diameter sized for slip fit into a corresponding hole in hinge arm 24 and an inner diameter sized to receive a bolt 27 with clearance, whereby the bolt and sleeve act as an adjustable shoulder screw allowing final adjustment of the position of carrier 22 prior to tightening of the bolt.

It will be apparent to those skilled in the art that other arrangements for magnetic biasing are possible. For example, the number and location of biasing magnets could be changed, and arrangements wherein a repelling magnetic force is used are possible. Moreover, the means for generating the magnetic force is not restricted to permanent magnets, and encompasses any means for generating a magnetic force, including electromagnets.

As can be appreciated from the foregoing description, the present invention helps provide reproducible positioning of exit surface 16A relative to sample surface 14A to establish a sample layer of consistently uniform thickness between the surfaces. The present invention is responsible for improving accuracy of refractive index readings from +/−0.0001 to +/−0.00005.

What is claimed is:
1. A prism assembly for a refractometer comprising:
   a sample prism having a sample surface for receiving a sample to be tested;
   an illumination prism having a light exit surface, said illumination prism being movable to and from a measurement position wherein said exit surface is opposite said sample surface and in contact with said sample; and
   magnetic biasing means for providing a magnetic force urging said sample surface and said exit surface toward one another to form sequential optical path transitions from said exit surface to said sample and from said sample to said sample surface when said illumination prism is in said measurement position.

2. The prism assembly according to claim 1, wherein said magnetic biasing means comprises at least one pair of cooperating magnets, one of said pair of magnets being fixed relative to said sample prism and another of said pair of magnets being fixed relative to said illumination prism.

3. The prism assembly according to claim 2, wherein said prism assembly includes a plurality of said cooperating magnet pairs.

4. The prism assembly according to claim 3, wherein said plurality of cooperating magnet pairs is distributed symmetrically about said exit surface and said sample surface.

5. The prism assembly according to claim 2, wherein said sample prism is fixed to a sample prism housing and said illumination prism is fixed to an illumination prism carrier, and said one of said pair of magnets is fixed to said sample prism housing and said another of said pair of magnets is fixed to said illumination prism carrier.

6. The prism assembly according to claim 1, wherein said magnetic force is one of attraction.

* * * * *